United States Patent
Sklar et al.

(10) Patent No.: US 6,453,111 B1
(45) Date of Patent: *Sep. 17, 2002

(54) INTERACTIVE WORKSTATION FOR CREATING CUSTOMIZED, WATCH AND DO PHYSICAL EXERCISE PROGRAMS

(75) Inventors: Joseph H. Sklar, Longmeadow; Gregory A. Green, Marlboro; Donald L. Graham, Longmeadow, all of MA (US); Geoff F. Elia, Somers, CT (US); Terry D. Ditmar; James F. Biron, both of Longmeadow, MA (US)

(73) Assignee: OmniMedia Systems Inc., Great Barrington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/391,639

(22) Filed: Sep. 7, 1999

Related U.S. Application Data

(63) Continuation of application No. 08/746,371, filed on Nov. 8, 1996, now Pat. No. 5,949,951.
(60) Provisional application No. 60/006,406, filed on Nov. 9, 1995.

(51) Int. Cl.[7] .......................... H04N 5/76; H04N 5/928; H04N 5/78
(52) U.S. Cl. ............................. 386/46; 386/55; 386/96
(58) Field of Search .......................... 386/46, 95, 96, 386/104, 107, 112, 124, 52, 54, 1, 39, 40, 4, 55; H04N 5/76, 5/928, 5/78

(56) References Cited

U.S. PATENT DOCUMENTS

| | | | |
|---|---|---|---|
| 5,065,345 A | 11/1991 | Knowles et al. | 395/154 |
| 5,189,563 A | 2/1993 | Breslau et al. | 360/14.1 |
| 5,227,892 A | 7/1993 | Lince | 358/335 |
| 5,237,648 A | 8/1993 | Mills et al. | 395/133 |
| 5,287,489 A | 2/1994 | Nimmo et al. | 395/500 |
| 5,301,172 A | 4/1994 | Richards et al. | 369/32 |
| 5,307,456 A | 4/1994 | MacKay | 395/154 |
| 5,331,474 A | 7/1994 | Lee | 360/13 |
| 5,333,061 A * | 7/1994 | Nakashima et al. | 386/46 |
| 5,355,132 A | 10/1994 | Kani et al. | 341/55 |
| 5,537,530 A | 7/1996 | Edgar et al. | 395/157 |
| 5,576,844 A | 11/1996 | Anderson et al. | 386/52 |
| 5,590,262 A | 12/1996 | Isadore-Barreca | 395/806 |
| 5,623,690 A | 4/1997 | Palmer et al. | 395/806 |

* cited by examiner

*Primary Examiner*—Robert Chevalier
(74) *Attorney, Agent, or Firm*—Pandiscio & Pandiscio

(57) ABSTRACT

An interactive touchscreen workstation is disclosed for generating patient-specific physical therapy videotapes. The workstation generally includes an appropriately programmed, digital central processing unit; first storage unit for storing digital video exercise data; second storage unit for storing digital audio exercise data; third storage unit for storing digital patient data; fourth storage unit for storing digital audio music data; user interface controls for directing the operation of the central processing unit so as to (i) generate a sequence of digital video frames from the data contained in the first storage unit, with that sequence corresponding to a particular physical therapy regimen prescribed for that patient, and (ii) generate a digital audio track from the digital audio exercise data contained in the second storage unit, and/or the digital audio music data contained in the fourth storage unit, with the digital audio track generated by the central processing unit corresponding to the sequence of digital video frames generated by the central processing unit; and output unit for recording the-sequence of digital video frames generated by the central processing unit and digital audio track generated by the central processing unit on a standard videotape, which videotape can thereafter be used by a patient to conduct "watch-and-do" physical therapy by playing back the videotape while simultaneously carrying out the regimen of physical therapy exercises specified in, and illustrated by, that same videotape.

3 Claims, 16 Drawing Sheets

| AVINAMEF | HEADER | EXNAME | ORDER | SETS | REST | HOLD | REPS | RANGE | SPEED |
|---|---|---|---|---|---|---|---|---|---|
| D:\V\TA04.AVI | ANKLE | ANKLE CIRCUMDUCTION | 1 | 1 | 20 | 0 | 0 | FULL | FULL |
| D:\V\TA01.AVI | ANKLE | ANKLE PUMPS | 2 | 1 | 30 | 0 | 0 | FULL | FULL |
| D:\V\TA16.AVI | ANKLE | DORSIFLEXION VS. BAND | 3 | 1 | 40 | 0 | 0 | FULL | FULL |
| D:\V\TA15.AVI | ANKLE | EVERSION VS. BAND | 4 | 1 | 50 | 0 | 0 | FULL | FULL |
| D:\V\TA07.AVI | ANKLE | EVERSION-ISOMETRIC | 5 | 1 | 60 | 0 | 0 | FULL | FULL |
| D:\V\TA02.AVI | ANKLE | EVERSION STRETCH | 6 | 1 | 70 | 0 | 0 | FULL | FULL |

SAMPLE "PLAY LIST" STACK

FIG. 6B

The RT System and RehabiliTapes are designed for the exclusive use of doctors and licensed therapists with knowledge of kinetic exercises for rehabilitative care.

This RehabiliTape has been specifically customized for

Patient Name Here and should not be used by any other person.

Omni Rehab Systems, Inc. is not responsible for the unauthorized production or use of any Rehabilitape.

Remember; if any exercise produces pain, the exercise should be discontinued immediately and you should contact your doctor or therapist before continuing the exercise program.

ALL RIGHTS RESERVED
©1995 Omni Rehab Systems, Inc.

FIG. 19

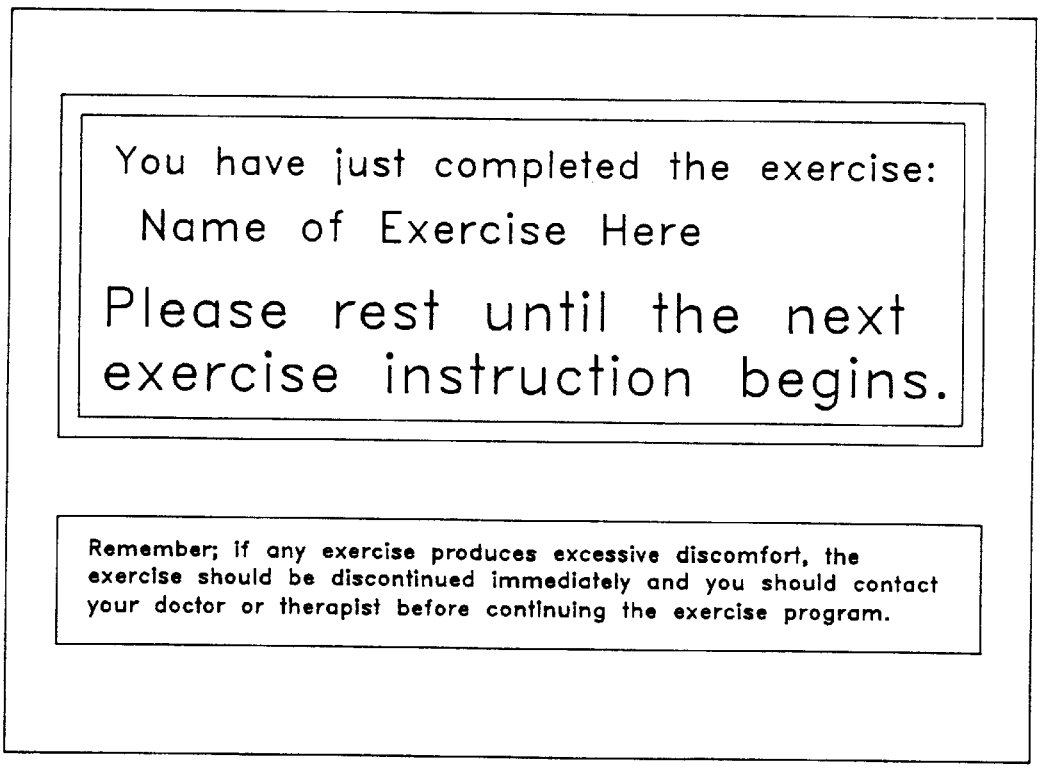

FIG. 20

INTERACTIVE WORKSTATION FOR CREATING CUSTOMIZED, WATCH AND DO PHYSICAL EXERCISE PROGRAMS

This is a continuation of U.S. patent application Ser. No. 08/746,371, now U.S. Pat. No. 5,949,951 filed Nov. 8, 1996 by Joseph H. Sklar, Gregory A. Green, Donald L. Graham, Geoff F. Elia, Terry D. Ditmar, and James F. Biron for INTERACTIVE WORKSTATION FOR CREATING CUSTOMIZED, WATCH AND DO PHYSICAL EXERCISE PROGRAMS (as amended).

This patent application claims benefit of pending prior U.S. Provisional Patent Application Ser. No. 60/006,406, filed Nov. 9, 1995 by Joseph H. Sklar et al. for INTERACTIVE TOUCHSCREEN WORKSTATION FOR GENERATING PATIENT-SPECIFIC PHYSICAL THERAPY VIDEOTAPES.

FIELD OF THE INVENTION

This invention relates to the provision of physical therapy in general, and more particularly to the provision of physical therapy using patient-specific videotapes.

BACKGROUND OF THE INVENTION

Physical therapy typically requires that a patient undertake a prescribed series of repetitive exercises so as to strengthen or otherwise treat a portion of that patient's body. These prescribed exercises are patient-specific, in the sense that they must take into account the general health of the patient, the specific therapy to be achieved, etc. Since the patient typically performs at least some of the exercises out of view of the therapist, it is common for the therapist to provide the patient with a set of written guidelines to be followed when carrying out the prescribed exercise regimen. Among other things, this set of written guidelines may include paper drawings of the exercises which are to be performed by the patient.

Unfortunately, it can be very difficult for the physical therapist to provide the patient with all of the desired instructions via the aforementioned written guidelines, even where these guidelines include paper drawings.

For one thing, it can be prohibitively time-consuming for the physical therapist to provide each individual patient with their own unique set of written instructions, where those instructions are perfectly tailored to the specific physical therapy regimen to be undertaken by that patient.

For another thing, in many cases it can be very difficult for the therapist to provide the patient with a set of written instructions which will provide all of the desired information to the patient. This may be due to the inherent difficulty of illustrating dynamic actions using static drawings, and/or due to patient miscomprehension of written instructions, etc.

In addition to the foregoing, many patients tend to find their prescribed exercises extremely boring, due to the highly repetitive nature of these exercises. As a result, some patients unilaterally shorten their exercise regimen, or they may even skip it altogether. This can significantly undermine the effectiveness of the physical therapy prescribed for that patient.

OBJECTS OF THE INVENTION

As a result, one object of the present invention is to provide a novel system for providing patient-specific physical therapy to a patient.

Another object of the present invention is to provide a novel method for providing patient-specific physical therapy to a patient.

And another object of the present invention is to provide a novel interactive touchscreen workstation for generating patient-specific physical therapy videotapes.

Still another object of the present invention is to provide novel, "watch-and-do" patient-specific physical therapy videotapes for use by a patient when carrying out a regimen of physical therapy exercises.

And another object of the present invention is to provide apparatus which can be used to prepare "watch-and-do" videotapes.

SUMMARY OF THE INVENTION

These and other objects of the present invention are achieved by the provision and use of a novel interactive touchscreen workstation which is adapted to generate patient-specific physical therapy videotapes. The workstation generally includes an appropriately programmed, digital central processing unit; first storage means for storing digital video exercise data; second storage means for storing digital audio exercise data; third storage means for storing digital patient data; fourth storage means for storing digital audio music data; user interface controls for directing the operation of the central processing unit so as to (i) generate a sequence of digital video frames from the digital video exercise data contained in the first storage means, with that sequence corresponding to a particular physical therapy regimen prescribed for that patient, and (ii) generate a digital audio track from the digital audio exercise data contained in the second storage means, and/or the digital audio music data contained in the fourth storage means, with the digital audio track generated by the central processing unit corresponding to the sequence of digital video frames generated by the central processing unit; and output means for recording the sequence of digital video frames generated by the central processing unit, and the digital audio track generated by the central processing unit, on a standard videotape. The videotape can thereafter be used by a patient to conduct "watch-and-do" physical therapy, i.e., by playing back the videotape while simultaneously carrying out the regimen of physical therapy exercises specified in, and illustrated by, that same videotape.

In another form of the invention, an interactive touchscreen workstation is provided for generating "watch and do" videotapes, the workstation comprising a programmed, digital central processor; first storage means for storing digital video data; second storage means for storing digital audio data; user interface controls for directing the operation of the central processor so as to (i) generate a sequence of digital video frames from the data contained in the first storage means, in a sequence corresponding to a particular physical activity which is to be depicted in the "watch-and-do" videotape, and (ii) generate a digital audio track from the digital audio data contained in the second storage means in synchronized relation to the sequence of digital video frames generated by the central processing unit; and output means for synchronously recording the sequence of digital video frames generated by the central processing unit, and the digital audio track generated by the central processing unit, on a standard videotape.

BRIEF DESCRIPTION OF THE DRAWINGS

These and other objects and features of the present invention will be more fully disclosed in, or rendered obvious by, the following detailed description of the preferred embodiment of the invention, which is to be considered together with the accompanying drawings wherein like numbers refer to like parts and further wherein:

FIG. 6B is a sample "play list" stack of the sort generated during operation of the system;

FIGS. 19 and 20 illustrate various screen displays which may be recorded on the videotape for subsequent viewing by a patient.

DETAILED DESCRIPTION OF THE PREFERRED EMBODIMENT

This patent application claims benefit of pending prior U.S. Provisional Patent Application Ser. No. 60/006,406, filed Nov. 9, 1995 by Joseph H. Sklar et al. for INTERACTIVE TOUCHSCREEN WORKSTATION FOR GENERATING PATIENT-SPECIFIC PHYSICAL THERAPY VIDEOTAPES.

Figure 1:
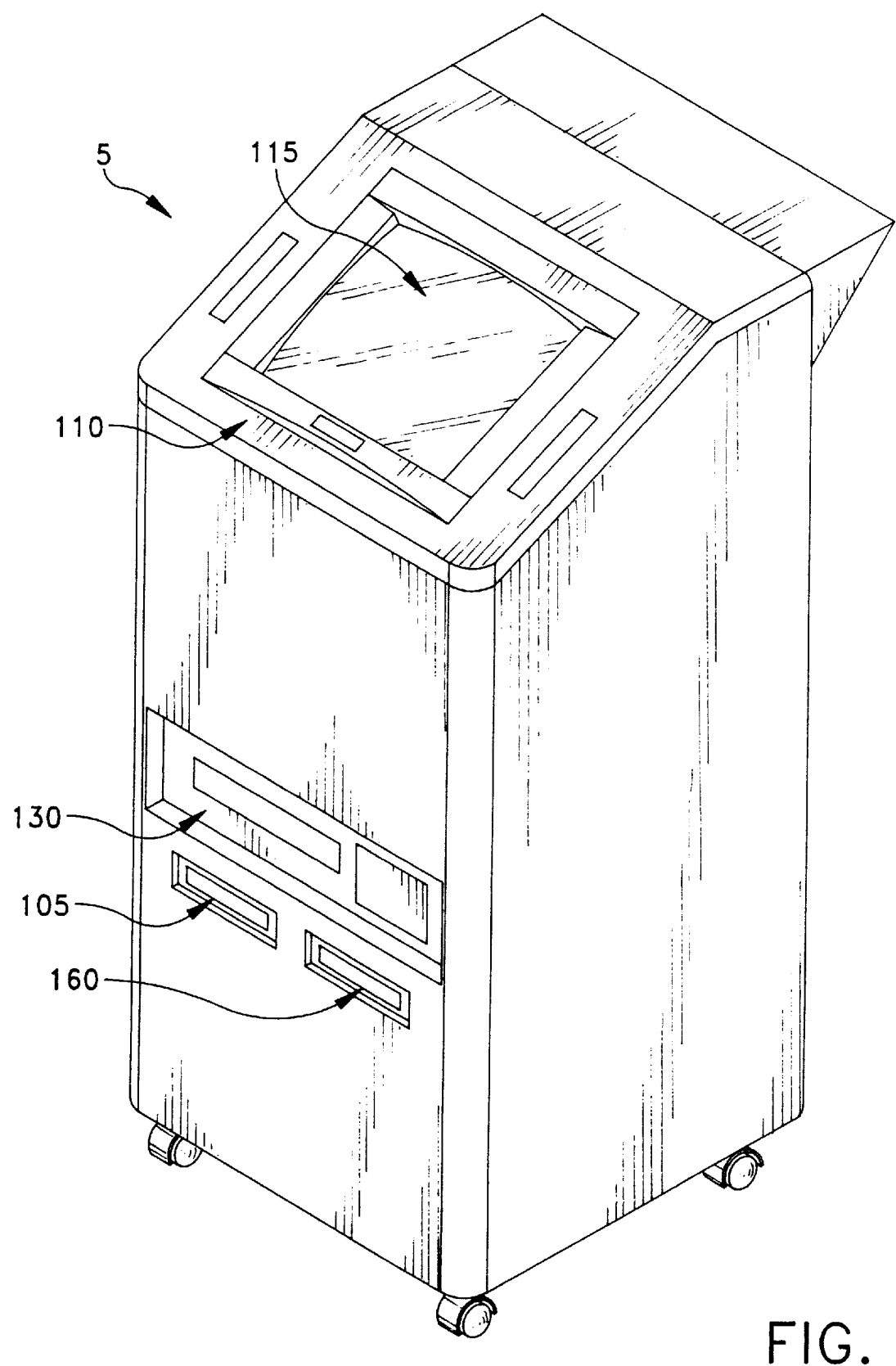
FIG. 1 is a perspective view of an interactive touchscreen workstation formed in accordance with the present invention.
Figure 2:
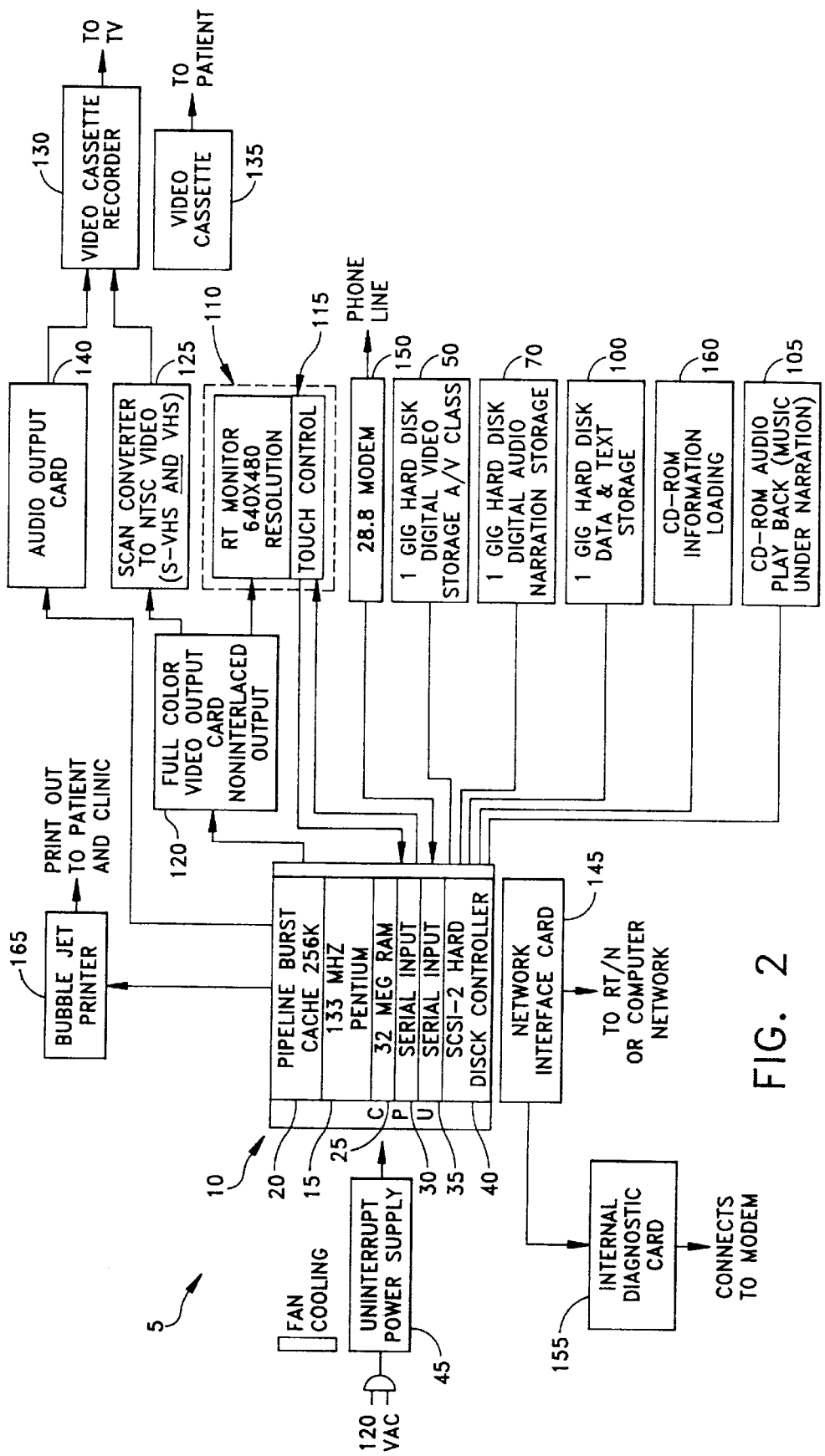
FIG. 2 is a schematic diagram illustrating the various components of the interactive touchscreen workstation shown in FIG. 1.

Looking first at FIGS. 1 and 2, there is shown an interactive touchscreen workstation 5 formed in accordance with the present invention.

Workstation 5 comprises an appropriately programmed, digital central processing unit ("CPU") 10. Preferably central processing unit 10 comprises a 133 MHz, Pentium-type microprocessor 15, a 256K pipeline burst cache 20, 32 MEG of RAM 25, a first serial port 30, a second serial port 35, and a SCSI-2 hard disk controller 40. Preferably an uninterrupted power supply 45 is used to supply power to central processing unit 10 and the remainder of workstation 5.

Figure 3:
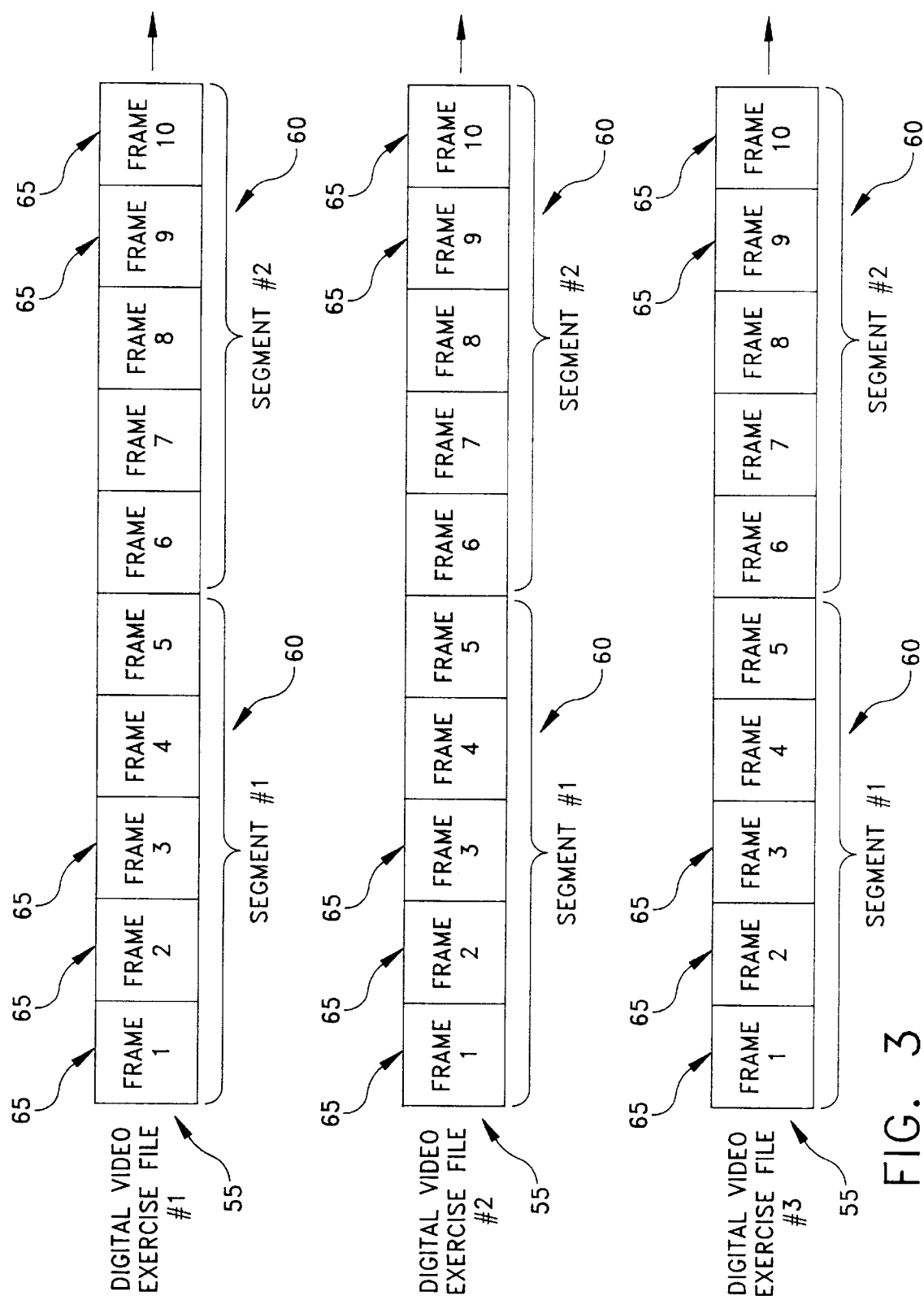
FIG. 3 is a schematic diagram illustrating how digital video exercise data is stored in files in the first storage means.
Figure 4:
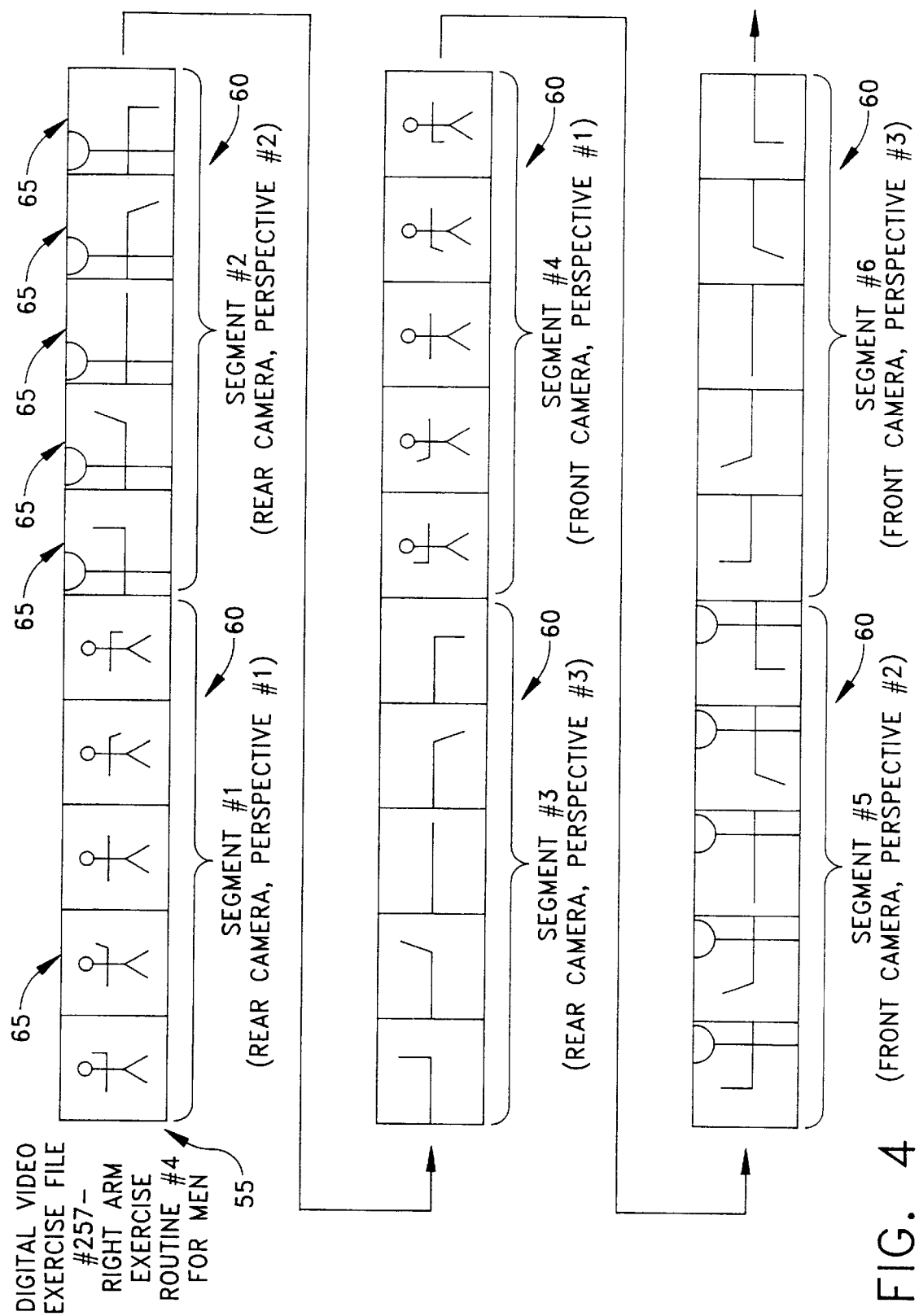
FIG. 4 is a schematic diagram illustrating how digital video exercise data is stored in a particular file in the first storage means.

A first storage means 50 is provided for storing digital video exercise data, e.g., video images of a person performing an exercise. Preferably first storage means 50 comprises a 1 GIG hard disk drive connected to hard disk controller 40. As seen in FIGS. 3 and 4, the digital video exercise data stored in first storage means 50 is organized in the form of a plurality of different files 55, where each file 55 relates to a different exercise. Each file 55 is in turn made up of a plurality of different segments 60, where each segment 60 relates to the same exercise, but is taken from a different camera perspective. Each segment 60 is in turn made up of a plurality of different frames 65, where each frame 65 provides one of the sequence of images required to make up moving video. Thus, each file 55 comprises multiple segments 60 of the same patient anatomy going through the same dynamic motion, with each segment 60 being taken from a different camera perspective.

By way of example but not limitation, a given file 55 might relate to a particular exercise routine for the right arm of a middle-aged male; and that given file 55 might comprise six different segments 60 to illustrate six different camera perspectives of the anatomy going through that particular exercise routine; and each segment 60 might in turn comprise 150 different frames 65 to illustrate anatomical movement.

In accordance with the present invention, any one of the frames 65 can be accessed from a given file 55, at any given time, in or out of the sequence shown in FIGS. 3 and 4. Furthermore, any one of the aforementioned frames 65 can be reaccessed (i.e. repeated) any number of times that may be desired.

In accordance with the present invention, the "starting" and "stopping" points of each segment 60 are carefully coordinated with the "starting" and "stopping" points of every other segment 60 in the same file 55, whereby different segments 60 taken from the same file can be intermixed with one another in a highly coordinated fashion, as will hereinafter be described in further detail. In particular, it has been recognized that, by rendering each segment 60 with a pre-defined modular format, a relatively small number of different segments 60 taken from the same file 55 can be assembled together in a wide variety of different ways so as to create the illusion of a single, large, non-repetitive, unique video creation which will effectively hold the patient's interest as that patient simultaneously watches the video and performs a repetitive series of physical therapy exercises.

In other words, it has been recognized that if a patient watches the exact same video scene twenty times in a row while doing a series of twenty identical anatomical movements, the patient will rapidly become bored with the procedure. However, if the patient watches a mixed program showing the very same twenty anatomical motions taken from a variety of different camera perspectives, the patient's interest can be maintained during the procedure. The highly modular nature of the segments 60 permits this to be easily achieved.

Also in accordance with the present invention, it is preferred that each segment 60 comprise only those frames 65 which are needed to represent anatomical movement in a single (e.g., forward) direction. This is because it has also been recognized that the constituent frames 65 making up a particular segment 60 can be sequenced in a reversed order (e.g., backward) so as to provide the reverse of the anatomical movement originally captured by the original sequence of those very same frames. Thus, by initially creating a given segment 60 using only those frames 65 needed to represent anatomical movement in a first direction, and thereafter playing back those very same frames first in their normal sequence and then in their reversed sequence, it is possible to represent anatomical movement in a first direction and then in a second direction, while storing only half the total number of frames ultimately played back to the patient.

Thus it will be seen that a single, large, non-repetitive, unique video creation can be assembled from the basic "building blocks" of digital video exercise data (e.g., frames 65 organized into segments 60) contained in first storage means 50. Furthermore, it will be seen that the manner in which this digital video exercise is stored permits the creation of extensive video works using a minimum of storage space. It will be appreciated that this is an important advantage when one considers the relative size of a single frame of video data, the number of camera perspectives to be stored, the number of exercises to be covered, etc.

Figure 5:
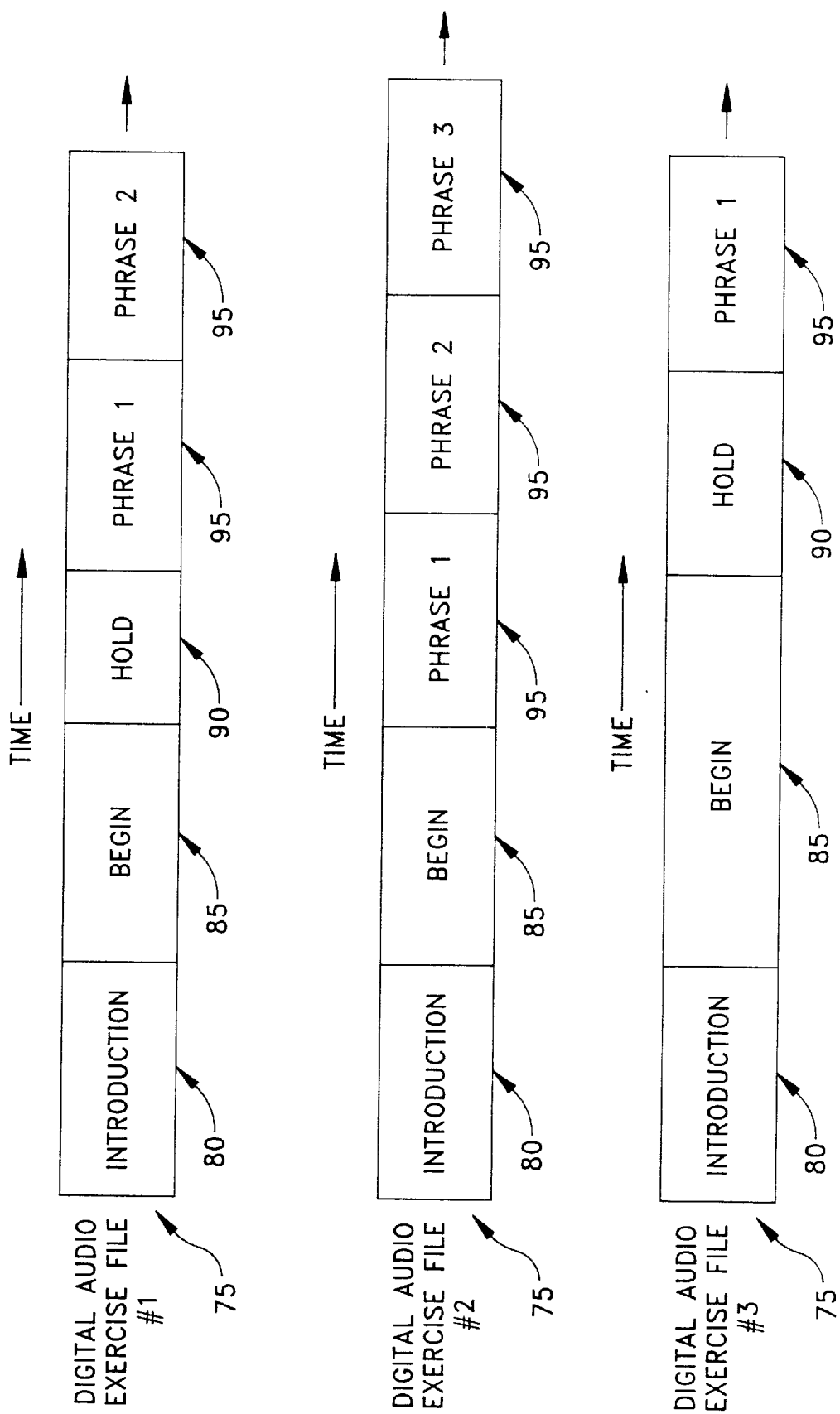
FIG. 5 is a schematic diagram illustrating how the digital audio exercise data is stored in files in the second storage means.

Returning now to FIG. 2, a second storage means 70 is provided for storing digital audio exercise data, e.g., verbal narration to accompany a person performing an exercise. Preferably second storage means 70 comprises a 1 GIG hard disk drive connected to hard disk controller 40. As seen in FIG. 5, the digital audio exercise data stored in second storage means 70 is organized in the form of a plurality of different files 75, where each file 75 relates to a different exercise. Each file 75 is in turn generally made up of several different sections. First there is an introduction narration section 80, then a "begin" or "start" narration section 85, next a "hold" narration section 90 (this section is optional, depending on the nature of the exercise), and finally one or more "phrases" narration sections 95. The introduction narration section 80 which can be used to introduce an exercise; the "begin" or "start" narration section 85 can be used to initiate the exercise; the "hold" narration section 90 can be used to accompany the "hold" phase of an exercise, to the extent that the exercise includes a "hold" phase; and the "phrases" narration sections 95 can be used to accompany various exercise scenes. In accordance with the present invention, any one of the sections 80, 85, 90 and 95 can be accessed from a given file 75, at any given time, in or out of the sequences shown in FIG. 5. Furthermore, any one of the aforementioned sections 80, 85, 90 and 95 can be re-accessed (i.e., repeated) any number of times that may be desired.

Returning again to FIG. 2, there is shown a third storage means 100 for storing digital patient data, e.g., text or other information associated with the patient undergoing the physical therapy treatment. By way of example, third storage means 100 might hold the patient's name, sex, date of birth, medical information, appointment information, physical therapy prescription, etc. Preferably third storage means 100 comprises a 1 GIG hard disk drive connected to hard disk controller 40. The digital patient data stored in third storage means 100 can be organized in any format easily recognized by the operating system and application program running on central processing unit 10.

Preferably, third storage means 100 also stores the operating system software and application program software used to control central processing unit 10.

By way of example, but not limitation, central processing unit 10 preferably operates under the Windows 95 operating system, and the application program controlling central processing unit 10, and the various system components, are all adapted so as to be compatible with this operating system. Video processing operates using a subset of the audio-video-interleave (AVI) standard designed to be compatible with the Windows 95 operating system. The AVI format provides the capability to control forward and reverse play back speed variation of the digital video components.

Looking next at FIGS. 1 and 2, workstation 5 also comprises fourth storage means 105 for storing digital audio music data, e.g., a background music soundtrack which is to be laid down on the videotape produced by the workstation. Preferably fourth storage means 105 comprises a CD-ROM audio playback unit connected to hard disk controller 40.

Figure 6:
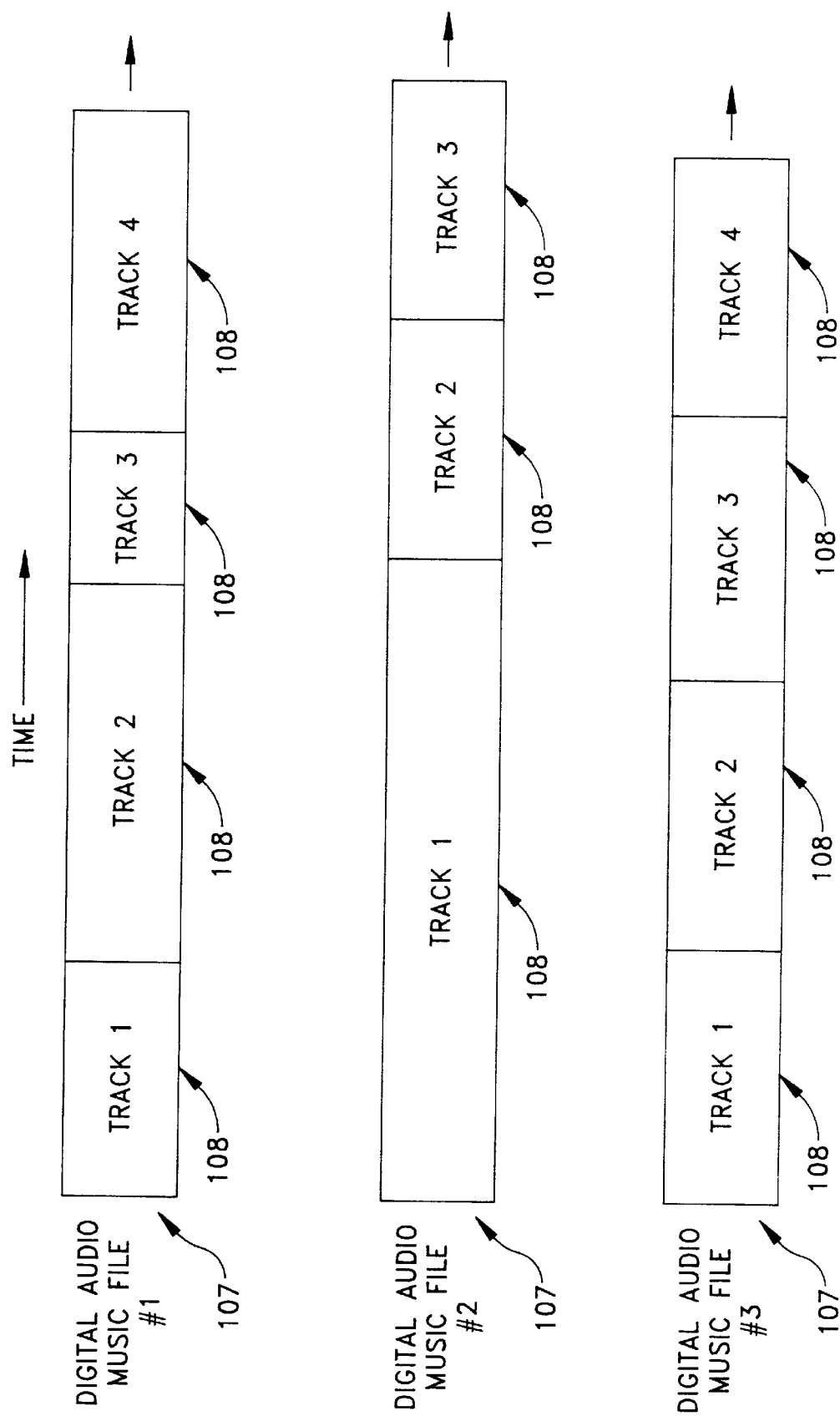
FIG. 6 is a schematic diagram illustrating how digital audio music data is stored in files in the fourth storage means.

As seen in FIG. 6, the digital audio music data stored in fourth storage means 105 is organized in the form of a plurality of different files 107. Each file 107 is in turn generally made up of a plurality of different tracks 108. In accordance with the present invention, any one of the tracks 108 can be accessed from a given file 107, at any time, in or out of the sequences shown in FIG. 6. Furthermore, any one of the aforementioned tracks 108 can be re-accessed (i.e., repeated) any number of times that may be desired.

Still looking at FIGS. 1 and 2, workstation 5 also comprises user interface controls 110 for allowing an operator to direct the operation of central processing unit 10, e.g., to allow a physical therapist to operate workstation 5. Preferably user interface controls 110 comprise a touchscreen display 115 of the sort well known in the art, whereby the user can review video images displayed on the touchscreen display and provide instructions back to central processing unit 10 by touching selected portions of that display. Touchscreen display 115 is connected to both central processing unit 10 and a video output card 120 as will hereinafter be discussed below, whereby the touchscreen display can receive video images from central processing unit 10 (via video output card 120) and return user instructions to central processing unit 10.

Referring now to FIG. 2, workstation 5 also comprises a full color video output card 120 of the sort well known in the art for providing non-interlaced video output. The video output generated by video output card 120 is in a form satisfactory to drive touchscreen 115. The input to video output card 120 is connected to central processing unit 10, whereby the video output card 120 can receive video output from central processing unit 10. The output from video output card 120 is connected to touchscreen display 115 and to a scan converter 125 as will hereinafter be discussed below.

Workstation 5 also comprises a scan converter 125 of the sort well known in the art for converting the output of video output card 120 into the NTSC video signal format (both VHS and S-VHS), whereby the output of that scan converter can be viewed on a standard television or captured on a standard video cassette recorder.

Looking next at FIGS. 1 and 2, the output from scan converter 125 is connected as the video input to a video cassette recorder 130. Video cassette recorder 130 is of the sort well known in the art for recording video (and audio) content. Video cassette recorder 130 can be used to produce a videotape 135 which can be given to a patient for use in performing "watch-and-do" physical therapy regimens. The output from video cassette recorder 130 can also be displayed on an ordinary television (not shown). By way of example, a physical therapist preparing a patient-specific physical therapy videotape on workstation 5 might choose to monitor the program content on such a television while actually making the videotape.

Workstation 5 also comprises an audio output card 140 of the sort well known in the art for providing audio output. Audio output card 140 is connected to the audio input of video cassette recorder 130 whereby an audio track generated by central processing unit 10 can be laid down on a videotape 135 as that videotape is being recorded by video cassette recorder 130.

As seen in FIG. 2, workstation 5 also preferably comprises a network interface card 145 by which workstation 5 can be connected to a computer network (not shown), and a modem 150 by which workstation 5 can be connected to a remote device, e.g., another computer (not shown). Preferably, an internal diagnostic card 155 is also connected to both central processing unit 10 and modem 150, whereby any system failures detected by internal diagnostic card 155 can be reported to a remote monitoring site (not shown) through the modem.

Looking now at FIGS. 1 and 2, workstation 5 also preferably comprises a CD-ROM read unit 160 whereby new data can be loaded into the system.

Workstation 5 also preferably comprises a printer 165 for providing hard paper output for professional and/or patient use.

Workstation 5 also comprises appropriate operating system software and application program software so that a physical therapist can use user interface controls 110 to prepare a patient-specific videotape for use by a patient in performing "watch-and-do" physical therapy. As noted above, such operating system software and application program software is preferably stored in third storage means 100, whereby it can direct the operation of central processing unit 10.

Figure 6A:
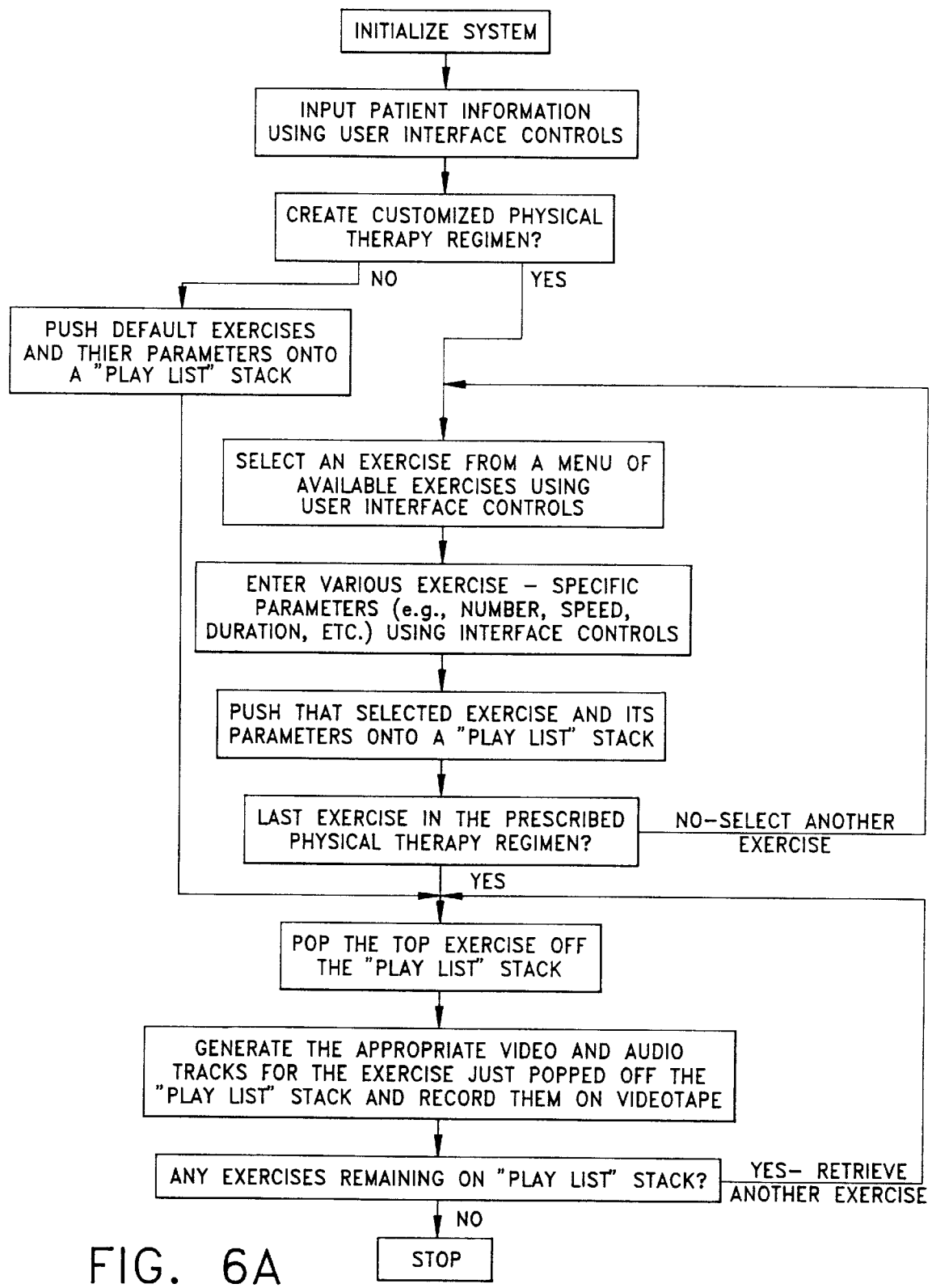
FIG. 6A is a flow chart illustrating operation of the system.

More specifically, and looking now at FIG. 6A, workstation 5 is programmed so that the physical therapist can use touchscreen display 115 to select the particular exercises which are to be performed by the patient in accordance with that patient's prescribed physical therapy regimen, and the particular number and sequence of those exercises. Workstation 5 is also programmed so that the physical therapist can use touchscreen display 115 to specify the appropriate parameters associated with each of the selected exercises, e.g., the number of repetitions which are to be performed, the hold duration for stretch exercises, the rest time between exercises, the range of motions for ballistic exercises, the speed of the exercise, etc. This information is stored in a "play list" stack, i.e., as each successive exercise routine is selected, it is "pushed" (along with its associated parameter information) onto the "play list" stack. A sample play list stack is shown in FIG. 6B. Alternatively, if the physical therapist prefers, a set of default exercises (and their respective parameters) can be selected, in which case the set of default exercises are "pushed" onto the "play list" stack.

Once the physical therapist has specified all of the exercises in the physical therapy regimen, and has identified the particular number and sequence of those exercises, and the relevant parameters for those exercises (i.e., once the "play list" stack has been created), the "play list" stack is read out one entry at a time and the videotape is created.

More particularly, for each successive exercise on the "play list" stack, the system accesses the digital video exercise data contained on first storage means 50 so as to generate an appropriate sequence of video frames for that exercise. This sequence of video frames corresponds exactly to the exercise procedure specified by the physical therapist using touchscreen display 115. Significantly, due to the highly modular format of the segments 60 stored in first storage means 50, a wide variety of different video sequences (taken from a variety of different camera perspectives) can be created for the repetitive cycles of the exercise then being "popped" off the "play list" stack, using a relatively small number of frames 65. In this respect it will be appreciated that the particular blend of segments 60 (i.e., the particular blend of different camera perspectives used to make up the repetitive cycles of the exercise then being "popped" off the "play list" stack) is specified in advance in the application program software.

The video stream created by the foregoing operation is recorded on videotape 135.

At the same time that the desired video stream is being laid down on videotape 135, the system also accesses the digital audio exercise data contained on second storage means 70 so as to generate a digital audio track corresponding to the various video sequences being assembled by the system. This digital audio track is also laid down on videotape 135 so as to accompany the video images being recorded.

Furthermore, the system also accesses the digital audio music data contained in fourth storage means 105 so as to lay down a background music soundtrack on videotape 135.

Figure 7:
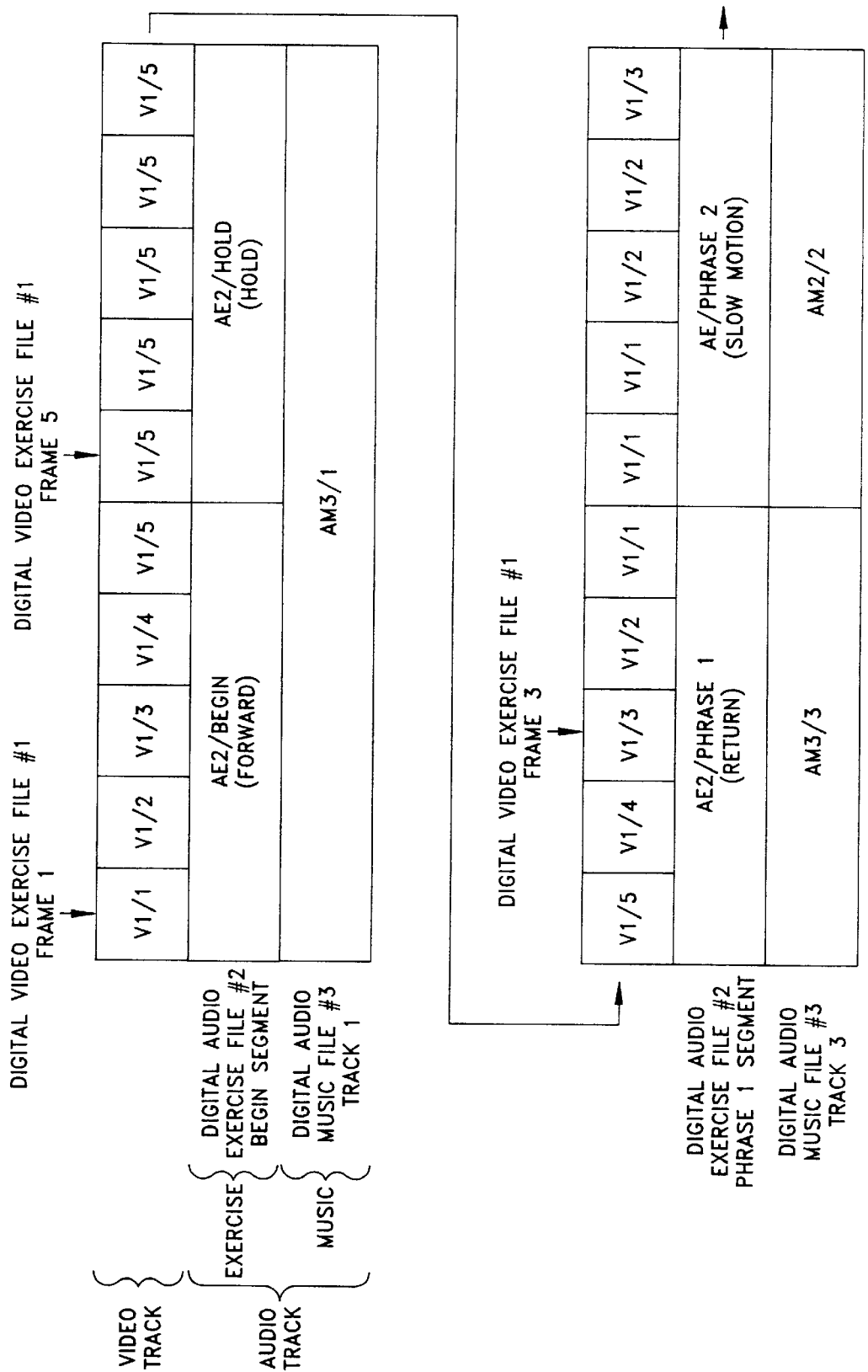
FIG. 7 is a schematic diagram illustrating how digital video exercise data, digital audio exercise data and digital audio music data can be combined so as to create the desired video and audio tracks for recording on a videotape.
Figure 8:
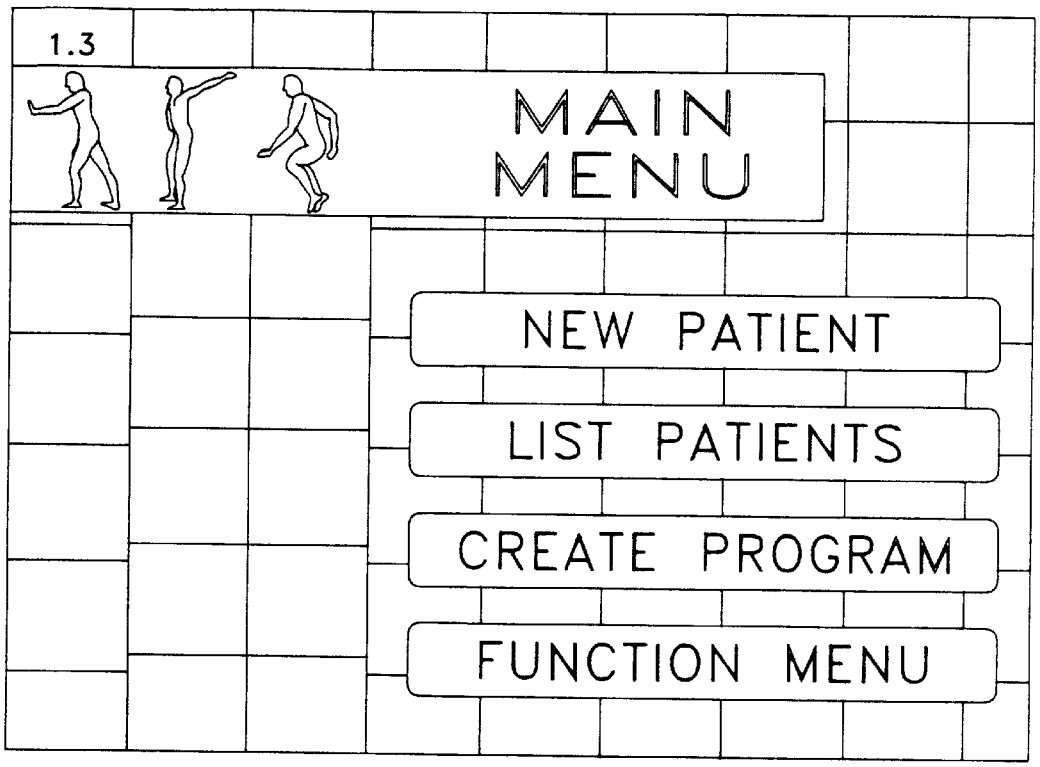
FIGS. 8–18 illustrate various screen displays presented to the physical therapist when creating a patient-specific physical therapy videotape using the interactive touchscreen workstation.
Figure 9:
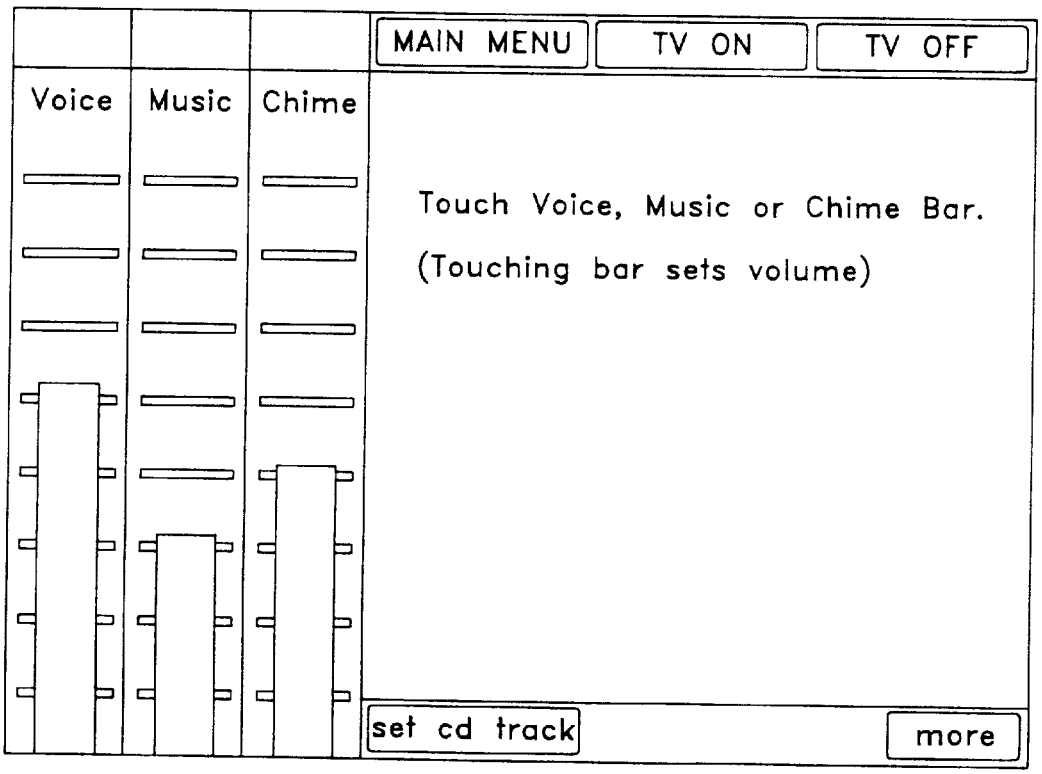
Figure 10:
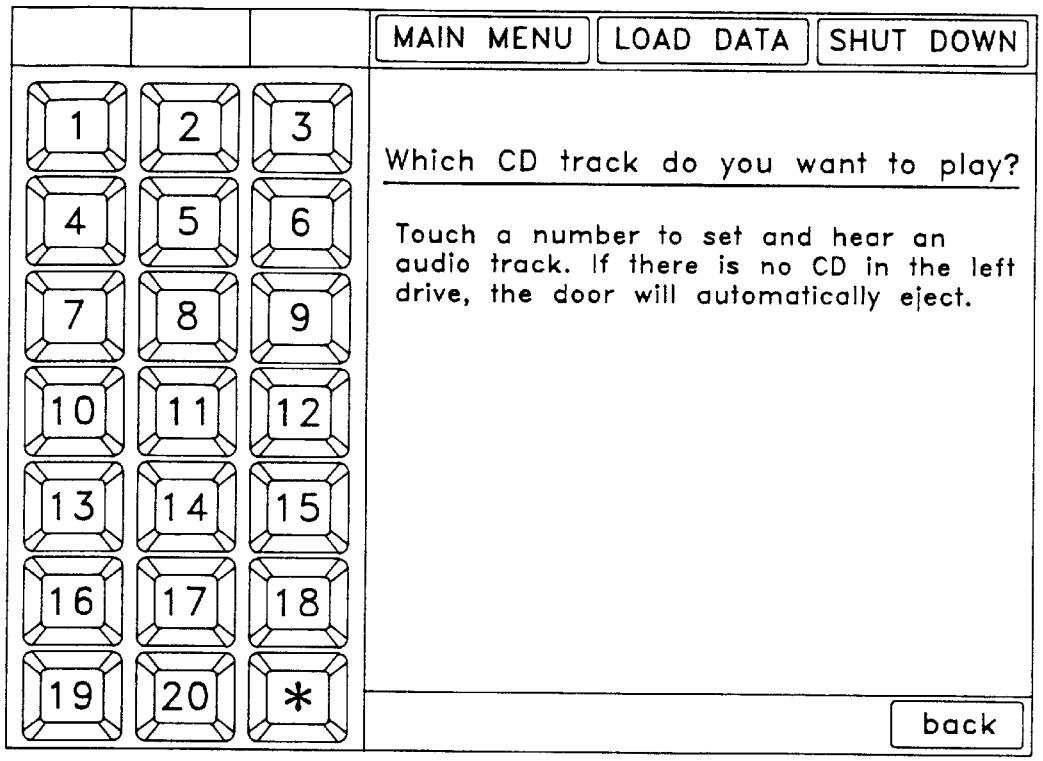
Figure 11:
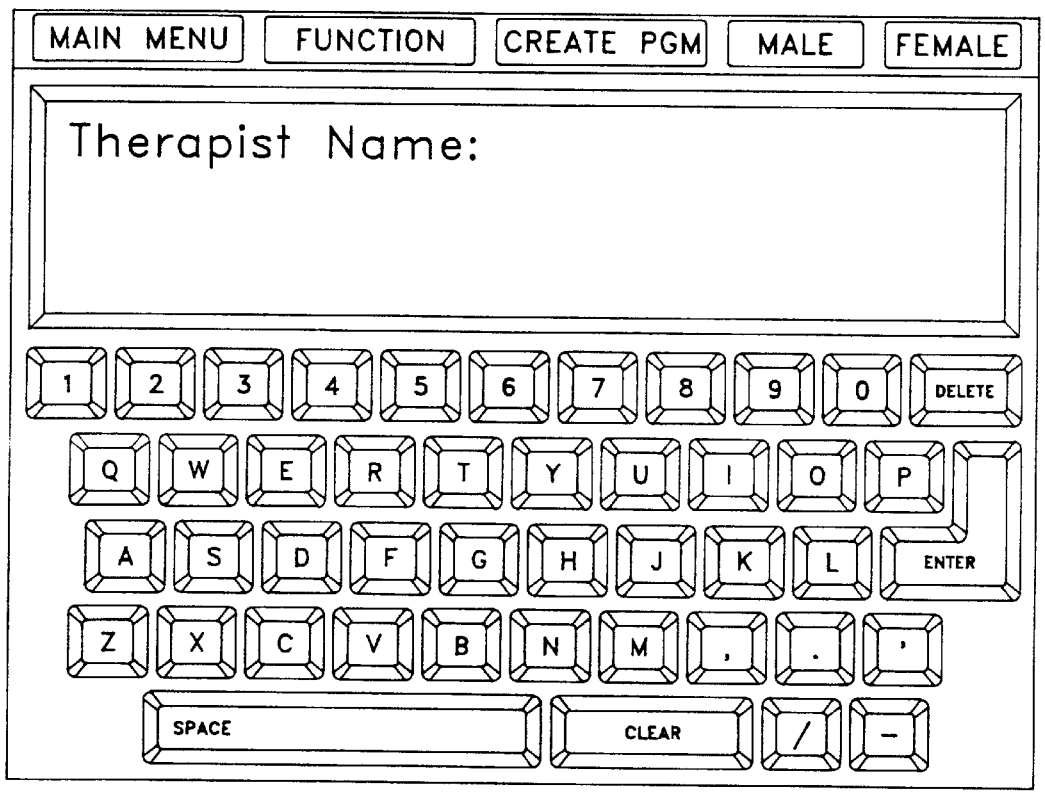
Figure 12:
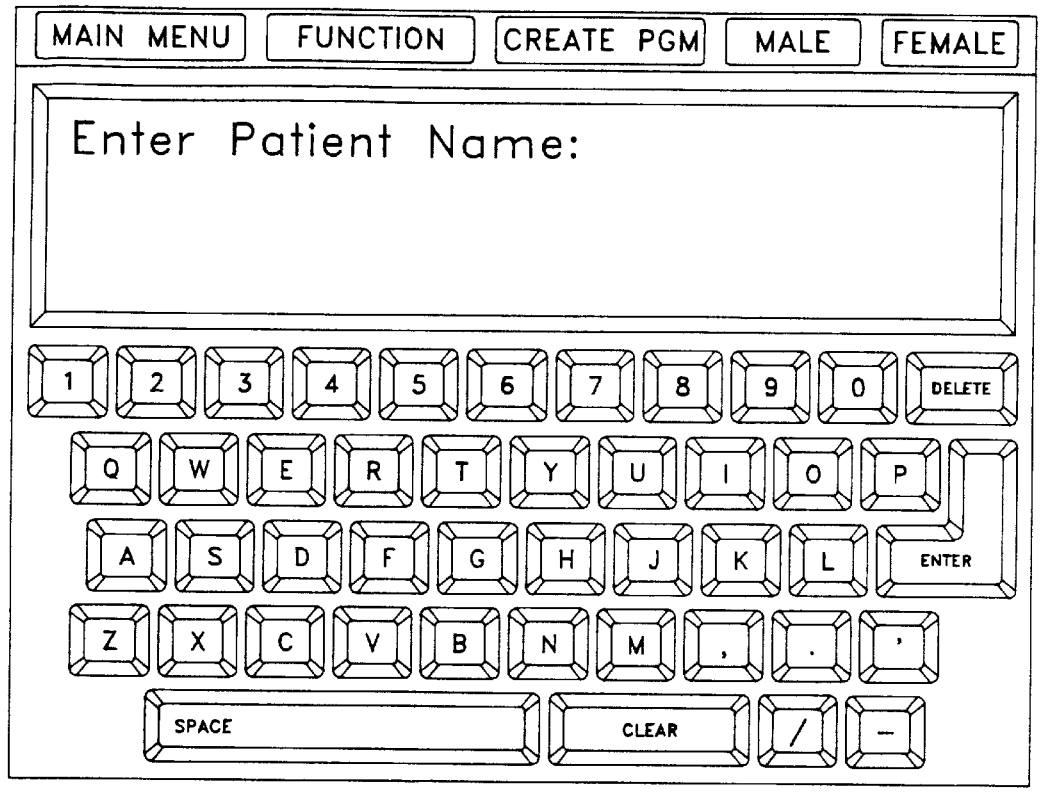
Figure 13:
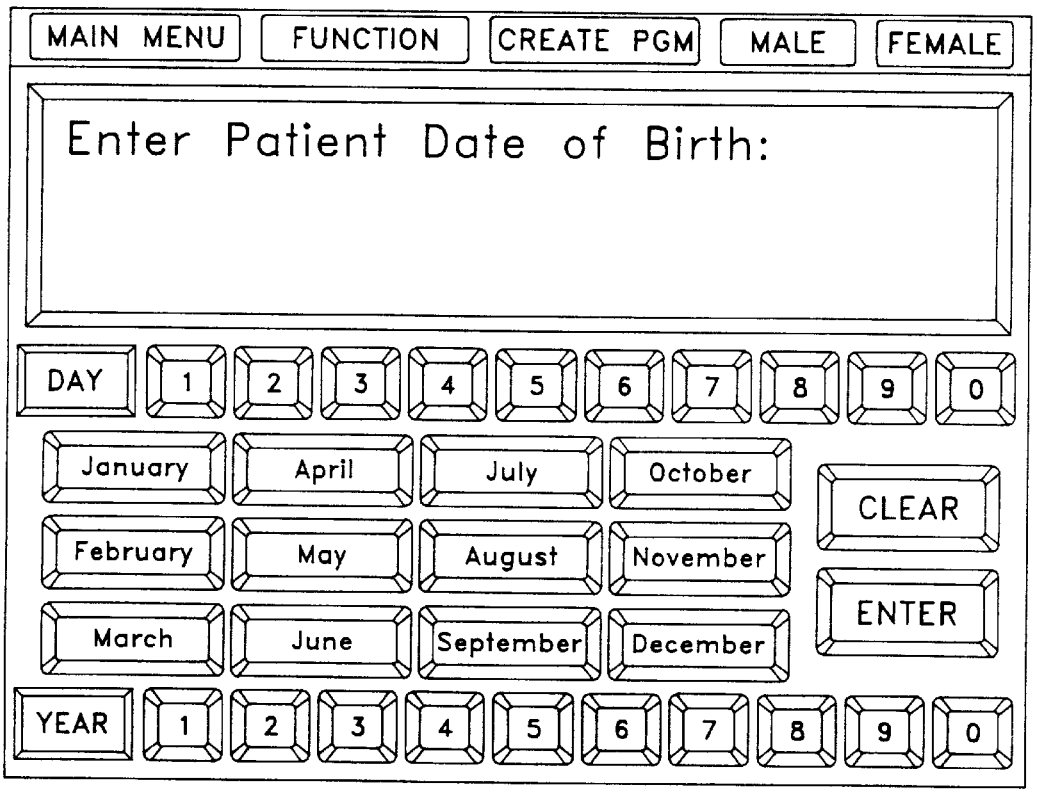
Figure 14:
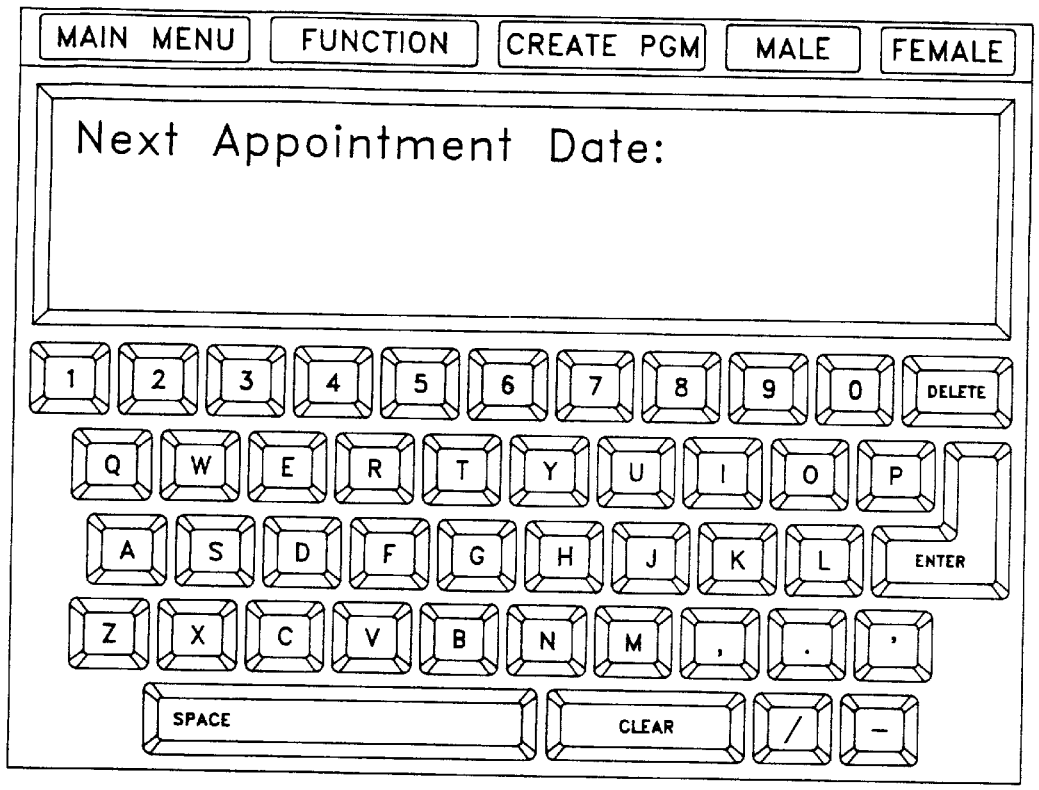
Figure 15:
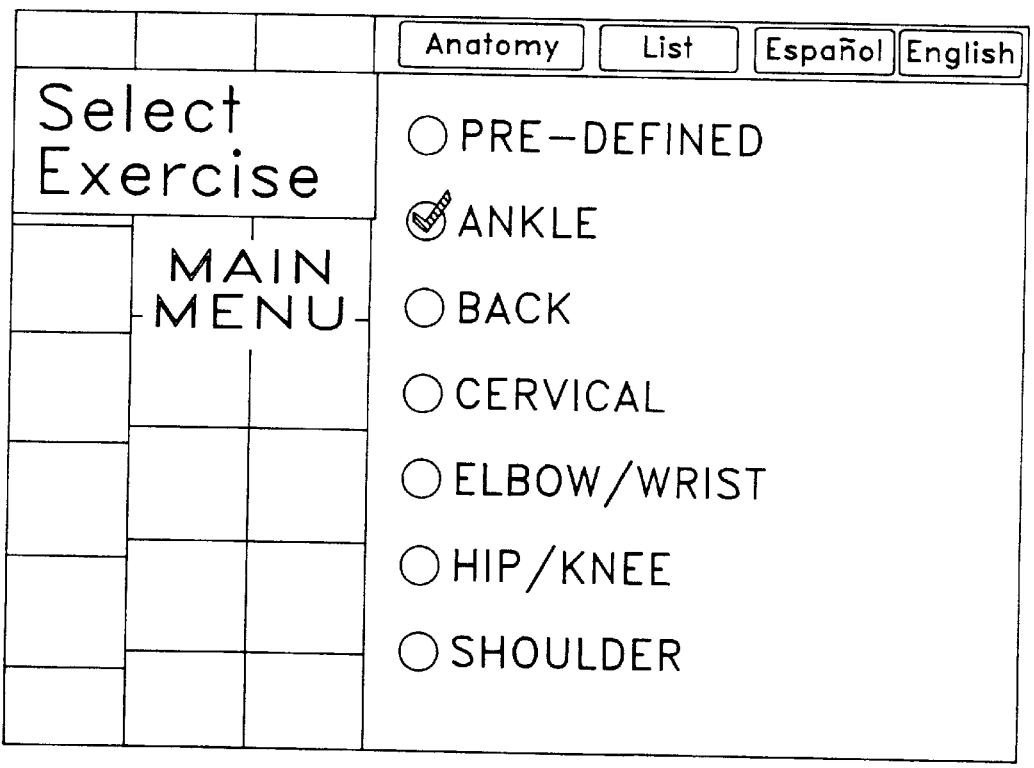
Figure 16:
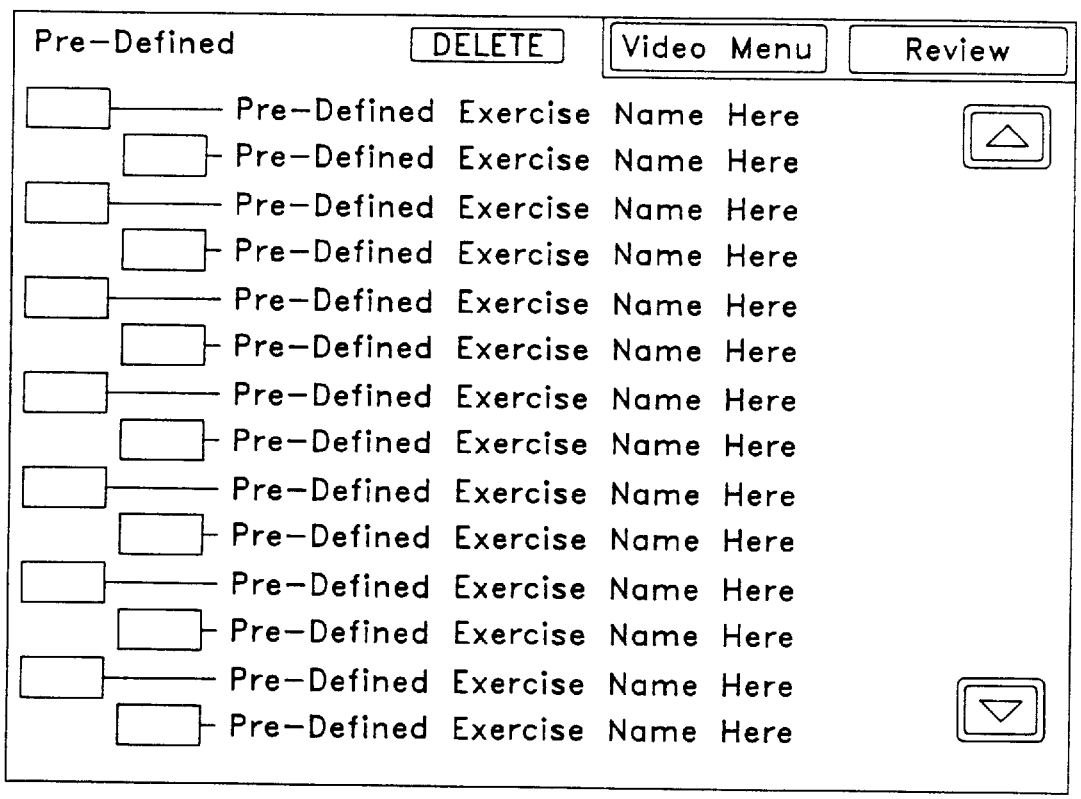
Figure 17:
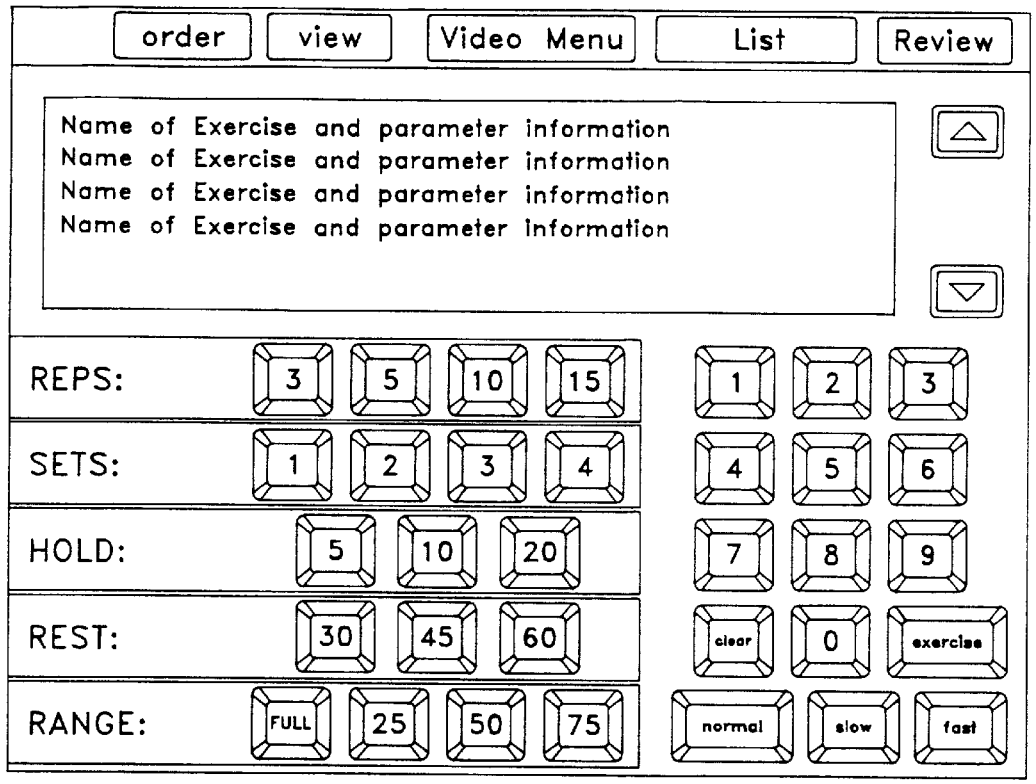
Figure 18:
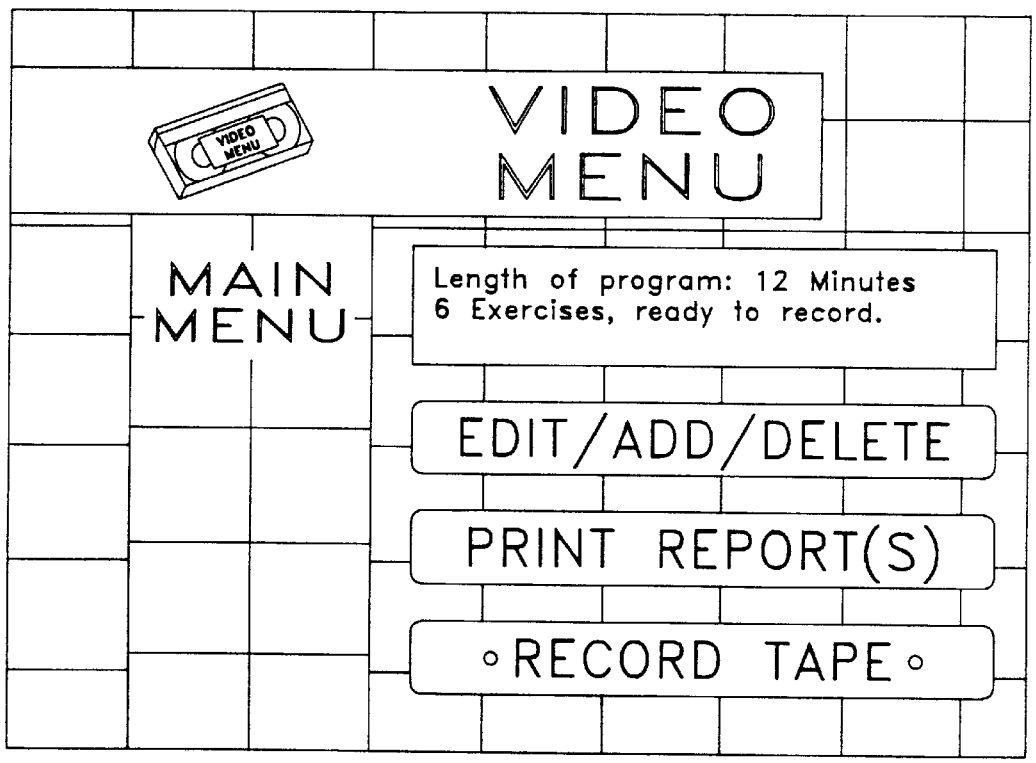

FIG. 7 illustrates how a sequence of video frames (taken from first storage means 50) can be combined in a variety of different ways so as to illustrate forward motion, a "hold" procedure, a return motion, and slow motion. FIG. 7 also illustrates how digital exercise audio data (taken from second storage means 70) and digital audio music data (taken from fourth storage means 105) can be laid down on videotape 135 in a coordinated fashion so as to complement the videotape's video content.

FIGS. 8–18 illustrate various displays which can be presented to the physical therapist so as to enable that therapist to create a patient-specific therapy program for the videotape.

FIGS. 19 and 20 illustrate other video displays which can be recorded on videotape 135 for viewing by the patient. The content of such text messages can be stored as video frames 55 in appropriate digital video files 55 in first storage means 50.

It is to be appreciated that inasmuch as each video segment 60 is designed to be seamlessly stitched together with every other video segment 60 contained within the same exercise file 55, many different video output sequences can be generated using a relatively small number of video segments 60. Thus the present invention has the ability to create the impression that the patient is continually viewing new material, when in fact the patient may simply be viewing the same video data in a continually-changing sequence. This feature can be utilized so as to provide a significantly more interesting therapy videotape. In addition, the corresponding modular format of the audio segments contained in second storage means 70 permits the creation of corresponding variations in the videotape's audio track.

Modifications Of The Preferred Embodiment

It is, of course, possible to modify the preferred embodiment described above without departing from the scope of the present invention.

By way of example, first storage means 50, second storage means 70 and third storage means 100 are described as preferably comprising three separate hard disk drives. However, it is possible for all three of these storage means to reside on a single hard disk drive.

Furthermore, whereas the present invention has been described above in the context of creating a patient-specific physical therapy videotape, it will also be appreciated that the present invention may be used to prepare "watch-and-do" videotapes for other purposes as well.

Advantages Of The Invention

Numerous advantages are achieved through the provision and use of the present invention.

For one thing, a novel system is disclosed for providing patient-specific physical therapy to a patient.

For another thing, a novel method is disclosed for providing patient-specific physical therapy to a patient.

And a novel interactive touchscreen workstation is disclosed for generating patient-specific physical therapy videotapes.

Also, novel "watch-and-do" patient-specific physical therapy videotapes can be provided for use by a patient when carrying out a regimen of physical therapy exercises.

And the present invention can be used to prepare "watch-and-do" videotapes.

What is claimed is:

1. A workstation for generating a "watch and do" audio-visual program and for recording the same on transportable, machine-readable media, said workstation comprising:

a central processor;

storage apparatus containing (1) video data representative of a pre-determined group of different physical activities, and (2) audio data related to said pre-determined group of different physical activities;

user interface controls for (1) permitting a user to select one of said different physical activities contained in said pre-determined group, (2) permitting the user to select a number of repetitions to be associated with said selected physical activity, and (3) directing the operation of said central processor so as to (a) generate a video track comprising a continuous sequence of video frames assembled from said video data contained in said storage apparatus, said continuous sequence of video frames depicting said selected number of repetitions of said selected physical activity, and (b) generate an audio track from said audio data contained in said storage apparatus, said audio track being associated with said video track; and an output device for synchronously recording said video and audio tracks as a continuous audio-visual track on the transportable, machine-readable media.

2. A workstation for generating a "watch and do" video program and for recording the same on transportable, machine-readable media, said workstation comprising:

a central processor;

storage apparatus for storing video data representative of a pre-determined group of different physical activities, said video data comprising at least one video segment, wherein each said video segment includes a plurality of video frames which together depict a selected half of said physical activity;

user interface controls for (1) permitting a user to select one of said different physical activities, and (2) directing the operation of said central processor so as to generate a sequence of video segments from said video data contained in said storage apparatus, said sequence comprising the video segment depicting a selected half of said selected physical activity, with that video segment being played first in one direction and thereafter in the opposite direction; and an output device for recording the sequence of video segments generated by said central processor as a continuous video track on the transportable, machine-readable media.

3. A workstation for generating a "watch and do" audio-visual program and for recording the same on transportable, machine-readable media, said workstation comprising:

a self-contained enclosure containing:

a central processor;

storage apparatus containing (1) video data representative of a pre-determined group of different physical activities, and (2) audio data related to said pre-determined group of different physical activities;

user interface controls for (1) permitting a user to select one of said different physical activities contained in said pre-determined group, (2) permitting the user to select a number of repetitions to be associated with said selected physical activity, and (3) directing the operation of said central processor so as to (a) generate a video track comprising a continuous sequence of video frames assembled from said video data contained in said storage apparatus, said continuous sequence of video frames depicting said selected number of repetitions of said selected physical activity, and (b) generate an audio track from said audio data contained in said storage apparatus, said audio track being associated with said video track; and an output device for synchronously recording said video and audio tracks as a continuous audio-visual track on the transportable, machine-readable media.

* * * * *